United States Patent
Shi et al.

(10) Patent No.: US 12,193,880 B2
(45) Date of Patent: Jan. 14, 2025

(54) MICROBUBBLE-BASED CONTRAST IMAGING USING PHASE SHIFT SYSTEMS AND METHODS

(71) Applicant: KONINKLIJKE PHILIPS N.V., Eindhoven (NL)

(72) Inventors: William Tao Shi, Wakefield, MA (US); Hua Xie, Cambridge, MA (US); Shiying Wang, Melrose, MA (US); Charles Tremblay-Darveau, Seattle, WA (US); Paul Sheeran, Woodinville, WA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 312 days.

(21) Appl. No.: 17/417,797

(22) PCT Filed: Jan. 6, 2020

(86) PCT No.: PCT/EP2020/050113
§ 371 (c)(1),
(2) Date: Jun. 24, 2021

(87) PCT Pub. No.: WO2020/141229
PCT Pub. Date: Jul. 9, 2020

(65) Prior Publication Data
US 2022/0071597 A1 Mar. 10, 2022

Related U.S. Application Data

(60) Provisional application No. 62/788,164, filed on Jan. 4, 2019.

(51) Int. Cl.
*A61B 8/08* (2006.01)
*A61B 8/00* (2006.01)
*G01S 7/52* (2006.01)

(52) U.S. Cl.
CPC ............ *A61B 8/481* (2013.01); *A61B 8/4488* (2013.01); *A61B 8/461* (2013.01); *A61B 8/54* (2013.01);
(Continued)

(58) Field of Classification Search
CPC ............ G01S 7/52039; G01S 7/52022; G01S 7/52085; A61B 8/481; A61B 8/4488
See application file for complete search history.

(56) References Cited

U.S. PATENT DOCUMENTS 6,171,246 B1    1/2001  Averkiou et al.
6,682,482 B1 *  1/2004  Krishnan ............ G01S 7/52039
                                                    600/443
(Continued)

FOREIGN PATENT DOCUMENTS

JP       4226882 B2 *   2/2009
WO     2005071437 A1    8/2005
(Continued)

OTHER PUBLICATIONS

Caskey E Tal: "Leveraging the Power of Ultrasound for Therapeutic Design and Optimizaiton"; Journal of Controlled Release, vol. 156, No. 3, Jul. 2011, pp. 297-306.
(Continued)

*Primary Examiner* — Joel Lamprecht
*Assistant Examiner* — Nyrobi Celestine

(57) ABSTRACT

The present disclosure describes ultrasound systems configured to perform microbubble-based contrast imaging with enhanced sensitivity. The systems can enhance echo signals derived from microbubbles while suppressing echo signals derived from tissue by detecting phase shifts exhibited by microbubbles in resonance. To detect the phase shifts, and thereby distinguish between microbubble-based signals and tissue-based signals, the systems can transmit a series of
(Continued)

ultrasound pulses into a target region in accordance with a predefined sequence. The sequence can include an initiation pulse configured to stimulate microbubbles into nonlinear oscillation, a detection pulse configured to detect the nonlinear oscillation, and a summation pulse formed by transmitting an initiation pulse and detection pulse with a small time delay therebetween. A signal processor included in the system can determine phase shifts exhibited by the signals generated in response to the series of pulses and mask non-microbubble-based signals based on the magnitude of the detected phase shifts.

17 Claims, 9 Drawing Sheets

(52) U.S. Cl.
CPC ...... *G01S 7/52022* (2013.01); *G01S 7/52039* (2013.01); *G01S 7/52085* (2013.01)

(56) References Cited

U.S. PATENT DOCUMENTS

| | | | |
|---|---|---|---|
| 2001/0034485 A1 | 10/2001 | Kawagishi et al. | |
| 2003/0181814 A1 | 9/2003 | Ji et al. | |
| 2004/0087857 A1* | 5/2004 | Napolitano | G01S 7/52046 600/443 |
| 2005/0273010 A1 | 12/2005 | Shi et al. | |
| 2007/0197916 A1* | 8/2007 | Kawagishi | G01S 7/52074 600/459 |
| 2009/0024031 A1* | 1/2009 | Ohuchi | G01S 15/8952 600/440 |
| 2015/0141830 A1* | 5/2015 | Kakee | A61B 8/5269 600/447 |
| 2019/0314001 A1* | 10/2019 | Maresca | G01S 7/52085 |

FOREIGN PATENT DOCUMENTS

| | | | | |
|---|---|---|---|---|
| WO | WO-2009072022 A1 * | 6/2009 | ............. | A61B 8/481 |
| WO | WO-2013104726 A1 * | 7/2013 | ............. | A61B 8/481 |

OTHER PUBLICATIONS

Quaia: Microbubble Ultrasound Contrast Agents:An Update; European Radiology, vol. 17, vol. 8, Mar. 2007, pp. 1995-2008.

Borsboom et al: "Pulse Subtraction Time Delay Imaging Method for Ultrasound Contrast Agent Detection"; IEEE Transactions on Ultrasonics, Ferroelectrics and Frequency Control, IEEE, vol. 56, No. 6, Jun. 2009, PPL. 1151-1158.

Tremblay-Darveau et al: "The Role of Microbubble Echo Phase Lag in Multipulse Ocntrast—Enhanced Ultrasound Imaging"; IEEE Transactions on Ultrasonics, Ferroelectrics and Frequency Control, IEEE, vol. 65, No. 8, Aug. 2018, pp. 1389-1401.

PCT/EP/2020/050113 ISR & Written Opinion, Apr. 29, 2020, 16 2020.

Siepmann et al: "Phase Shift Variance Imaging—A New Technique for Destructive Microbubble Imaging", IEEE Transactions on Ultrsonics, Ferroelectrics, and Frequency Control, vol. 60, No. 5, May 2013, pp. 909-923.

Simpson et al: "Pulse Inversion Doppler: a New Mehtod for Detecting Nonlinear Echoes From Microbubble Contrast Agents"; IEEE Transactions on Ultrasonics, Ferroelectrics, and Frequency Control, vol. 46, No. 2, Mar. 1999, pp. 372-382.

* cited by examiner

MICROBUBBLE-BASED CONTRAST IMAGING USING PHASE SHIFT SYSTEMS AND METHODS

CROSS-REFERENCE TO PRIOR APPLICATIONS

This application is the U.S. National Phase application under 35 U.S.C. § 371 of International Application No. PCT/EP2020/050113, filed on Jan. 6, 2020, which claims the benefit of U.S. Provisional Patent Application No. 62/788,164, filed on Jan. 4, 2019. These applications are hereby incorporated by reference herein.

TECHNICAL FIELD

The present disclosure pertains to ultrasound systems and methods for contrast imaging. Particular implementations involve systems configured to distinguish tissue-derived signals from microbubble-derived signals, and mask the tissue-derived signals to improve a signal-to-noise ratio associated with contrast-enhanced anatomy.

BACKGROUND

Contrast imaging often involves injecting contrast agents, e.g., microbubbles, intravenously into a patient and using ultrasound waves to detect the agents near targeted regions within the body. A unique characteristic of microbubble-based contrast agents is their resonance around a particular resonant frequency. As resonance is induced, each microbubble begins to oscillate in response to ultrasonic wave excitation. The oscillation amplitude may increase rapidly during the first few cycles of insonification before reaching a steady resonance stage with relatively constant, high oscillation amplitude that produces a strong, scattered nonlinear signal. A significant drawback of preexisting contrast imaging methods and/or ultrasound imaging systems, however, is the insufficient suppression of scattered or reflected signals received from surrounding tissues. New technologies are thus needed for identifying and removing linearly scattered or reflected signals derived from tissue, thereby enhancing the clarity of the remaining nonlinear signals produced by contrast microbubbles.

SUMMARY

The present disclosure describes systems and methods for ultrasound contrast imaging that maximize echo signals derived from highly nonlinear scatterers, e.g., microbubbles, while suppressing echo signals derived from primarily linear scatterers, e.g., non-microbubble sources such as tissue. Disclosed systems may include an ultrasound transducer equipped with an array of individual elements. The array can be configured to transmit a series of ultrasonic pulses into a region of interest (ROI) containing contrast agents, such as microbubbles. For ease of illustration, microbubbles will be referred to according to each of the examples described herein. The series of ultrasonic pulses can include an initiation pulse and a detection pulse that can each be transmitted individually, and a third pulse (referred to herein as the summation pulse) that can comprise a combined initiation pulse and detection pulse transmitted with a small delay therebetween. The initiation pulse can be configured to initiate the microbubbles into nonlinear oscillation, such as resonance, and the detection pulse, transmitted shortly after the initiation pulse, can be configured to continue to excite and also detect nonlinear oscillation of the resonant microbubbles caused by the initiation pulse. In some embodiments, the initiation pulse may be transmitted from separate array elements than the detection pulse. Each of the pulses may be imaged, such that ultrasound echoes embodying an initiation signal, a detection signal, and a summation signal are each acquired. A signal processor communicatively coupled with the ultrasound transducer can then detect phase shifts exhibited by the ultrasound echoes and selectively mask echoes with phase shifts falling below a specified threshold. Because the phase shifts may be significantly greater for nonlinear signals derived from microbubbles compared to the predominantly linear signals derived from tissue, the signal processor may thus be configured to utilize the detected phase shifts to accentuate the distinction between tissue-derived signals and microbubble-derived signals. After removing the noise or clutter in the form of tissue-based signals, the signal-to-noise ratio (SNR) of the remaining microbubble-based signals may be enhanced, thereby improving the sensitivity of the contrast imaging performed by the systems herein relative to preexisting systems.

In accordance with some examples of the present disclosure, an ultrasound imaging system may include an ultrasound transducer array configured to acquire echo signals responsive to a series of ultrasound pulses transmitted toward a target region containing microbubbles. The system may also include a controller configured to control the ultrasound transducer array to transmit the series of ultrasound pulses in accordance with a sequence. The sequence may include an initiation pulse configured to stimulate the microbubbles into resonance. The sequence may also include a summation pulse comprised of the initiation pulse and a detection pulse, where the detection pulse is transmitted after the initiation pulse and is configured to detect nonlinear oscillation signals of the microbubbles. The sequence may further include a second detection pulse transmitted alone. The system can also include one or more signal processors in communication with the ultrasound transducer array and configured to selectively mask non-microbubble-based signals generated in response to the initiation pulse.

In some examples, the processors are configured to selectively mask the non-microbubble-based signals by determining phase shifts exhibited by the echo signals. In some embodiments, determining the phase shifts exhibited by the echo signals involves comparing an initiation signal generated in response to the initiation pulse and a detection signal generated in response to the second detection pulse against a summation signal generated in response to the summation pulse. In some examples, the processors are configured to selectively mask the non-microbubble-based signals by applying a phase shift threshold to the phase shifts exhibited by the echo signals and masking echo signals exhibiting phase shifts below the threshold. In some embodiments, the phase shift threshold is about 10 degrees.

In some embodiments, the initiation pulse is transmitted from a first subset of elements of the ultrasound transducer array, and in some examples, the second detection pulse is transmitted only from a second subset of elements of the ultrasound transducer array that does not overlap with the first subset of elements. In some embodiments, the summation signal is transmitted from the first and second subsets of elements of the ultrasound transducer array.

In some examples, the second detection pulse is transmitted about 1 to 2 microseconds after the initiation pulse. In some embodiments, the system also includes an image processor configured to produce an ultrasound image of the target region based on the echo signals acquired by the ultrasound transducer array. In some examples, the system also includes a graphical user interface configured to display the ultrasound image of the target region. In various embodiments, the echo signals may include residual echo signals formed by imperfect coupling between non-overlapping elements of the ultrasound transducer array.

In accordance with some examples of the present disclosure, a method of ultrasound imaging involves transmitting a series of ultrasound pulses from an ultrasound transducer array toward a target region containing microbubbles and controlling the ultrasound transducer array to transmit the series of ultrasound pulses in accordance with a sequence. The sequence can include an initiation pulse configured to stimulate the microbubbles into resonance. The sequence can also include a summation pulse comprised of the initiation pulse and a detection pulse, where the detection pulse is transmitted after the initiation pulse and is configured to detect nonlinear oscillation signals of the microbubbles. The sequence can further include a second detection pulse transmitted alone. The method can also involve acquiring echo signals responsive to the series of ultrasound pulses and selectively masking non-microbubble-based signals generated in response to the initiation pulse.

In some examples, selectively masking non-microbubble-based signals involves determining phase shifts exhibited by the echo signals. In some embodiments, determining the phase shifts exhibited by the echo signals involves comparing an initiation signal generated in response to the initiation pulse and a detection signal generated in response to the second detection pulse against a summation signal generated in response to the summation pulse. In some examples, selectively masking non-microbubble-based signals involves applying a phase shift threshold to the phase shifts exhibited by the echo signals and masking echo signals exhibiting phase shifts below the threshold. In some embodiments, the initiation pulse is transmitted from a first subset of elements of the ultrasound transducer array, and in some examples, the second detection pulse is transmitted from a second subset of elements of the ultrasound transducer array that does not overlap with the first subset. In various examples, the method may further involve producing an ultrasound image of the target region based on the echo signals acquired by the ultrasound transducer array after selectively masking the non-microbubble-based signals.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
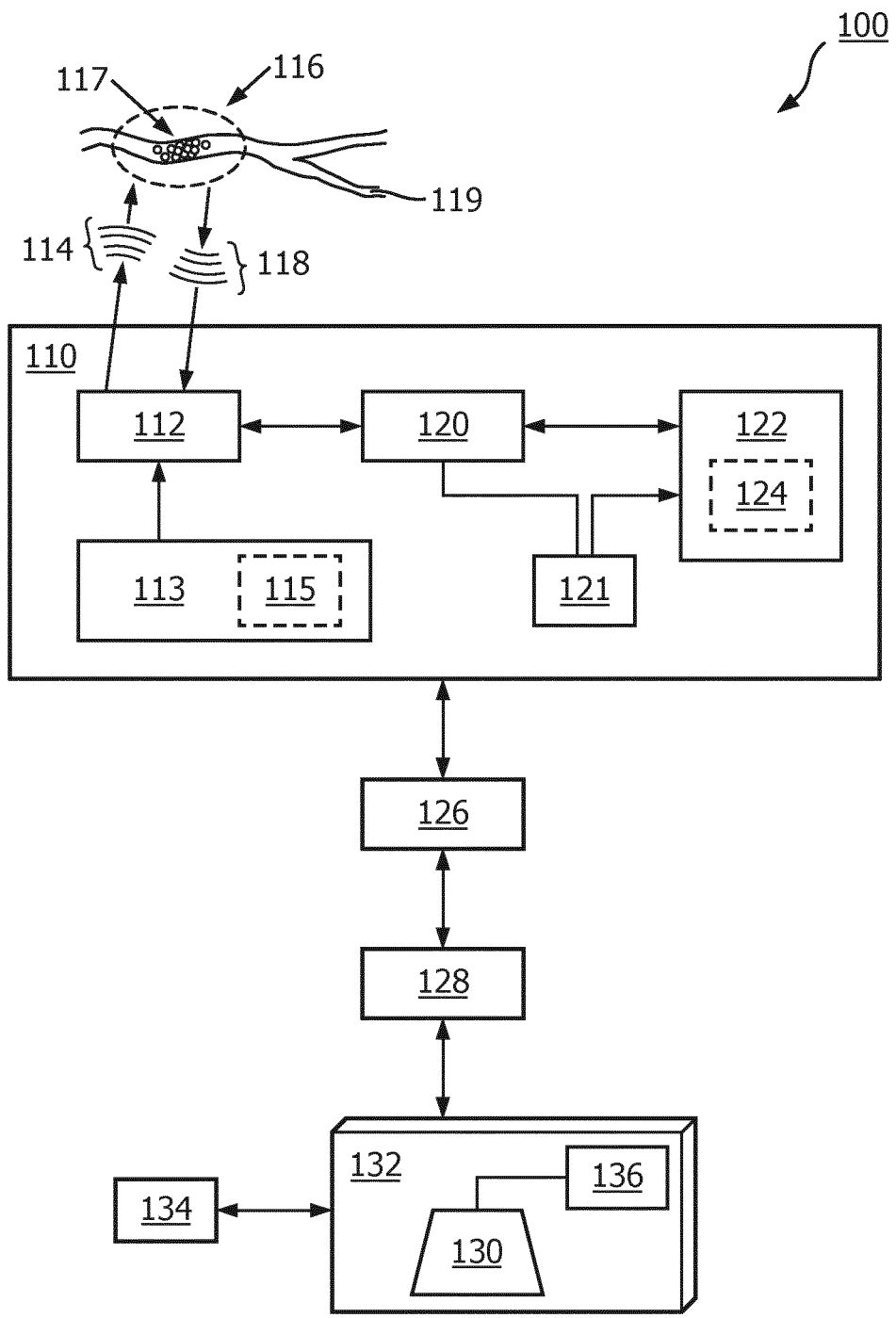
FIG. 1 is a block diagram of an ultrasound system in accordance with an embodiment of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Systems and methods herein involve microbubble-based, non-destructive contrast imaging of various target areas within a patient. The disclosed systems are configured to maximize the signals received from microbubbles, while suppressing the signals received from non-microbubble sources, e.g., tissue, such that contrast-enhanced anatomy is imaged with greater resolution and sensitivity. The systems can perform this function by detecting and utilizing the features of microbubbles that cause distinct echo signatures to be formed in response to insonification. Such features include the high contrast amplitude of resonant microbubbles and the significant phase shift that may occur as microbubbles are initiated into nonlinear oscillation in response to an ultrasound pulse. To observe these features, the disclosed systems may be configured to transmit an initiation pulse from select elements on a transducer array toward a region of a body that includes microbubble contrast agents. The initiation pulse can initiate the microbubbles into resonant oscillation. Subsequently, a detection pulse is transmitted from select elements on the transducer array to detect the resonant oscillation of the microbubbles. The significant phase shift that may occur upon achieving resonance can also be detected via separate transmission of an initiation pulse and a detection pulse. Because the phase shift exhibited by the microbubbles is typically much greater than the phase shift exhibited by other features, e.g., tissue, distinguishing microbubble-based signals from other signals may be improved by sorting received signals based on the phase shifts associated therewith. A phase mask can be applied to remove or suppress the tissue-derived signals, leaving only microbubble-based signals for further processing.

An ultrasound system in accordance with principles of the present disclosure may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, a beamform controller configured to direct beamform transmission and receipt of the beamformer, and a display configured to display, in some examples, ultrasound images generated by the ultrasound imaging system in B-mode and/or Doppler mode. The ultrasound imaging system may include one or more processors, which may be implemented in hardware and/or software components. The ultrasound system may include a display or graphics processor, which is operable to arrange the ultrasound images (2D, 3D, 4D etc.) and/or additional graphical information, which may include annotations, confidence metrics, user instructions, tissue information, patient information, indicators, color coding, highlights, and other graphical components, in a display window for display on a user interface of the ultrasound system. In some embodiments, the ultrasound images and associated measurements may be provided to a storage and/or memory device, such as a picture archiving and communication system (PACS) for post-exam review and reporting purposes.

FIG. 1 shows an example ultrasound system according to an embodiment of the present disclosure. The ultrasound system 100 may include an ultrasound data acquisition unit 110 configured to scan a two or three dimensional region of a body containing an ultrasonic contrast agent, e.g., microbubbles, with ultrasonic transmit beams. As each beam is transmitted along its steered path through the body, the beam returns echo signals with fundamental and (sub-, ultra- and super-) harmonic components corresponding to the transmitted frequency components. The echoes returned in response to the transmit signals may be modulated by the nonlinear response of the microbubbles encountered by the beam, thereby generating echo signals with nonlinear fundamental and harmonic components.

In the embodiment shown, the ultrasound data acquisition unit 110 includes an ultrasound probe equipped with an ultrasound sensor array 112 controlled by a controller 113. Under the direction of the controller 113, the array 112 can be configured to transmit a series of ultrasound pulses 114 in accordance with a sequence and having selected modulation characteristics into a region of interest (ROI) 116, which includes intravenously injected microbubbles 117, and receive ultrasound echoes 118 responsive to the transmitted pulses. The controller 113 can be responsive to a number of control parameters which determine the characteristics of the transmit beams or pulses 114, including the frequency components of the pulses, the pulse intensity and/or amplitude, the phase and/or polarity of the pulses, and/or the waveform profiles of the pulses. The controller 113 may also include a transmit waveform memory 115. Transmit waveforms with the desired characteristics can be designed and digitized and the digital samples stored in the transmit waveform memory 115. The control parameters may then address the memory 115 to select a desired transmit waveform, which can then be played out of the memory through a digital-to-analog converter, which produces the analog waveform. The analog waveform can be amplified and applied to the elements of the array 112.

The specific properties of the microbubbles 117 may vary. In some embodiments, the microbubbles 117 may have a diameter ranging from about 1 μm to about 5 μm, about 2 μm to about 3 μm, or about 2.65 μm. The thickness and shear viscosity of the microbubbles 117 may also vary. For example, the microbubble thickness may range from about 1 to about 8 nm, about 2 to about 6 nm, or about 4 nm. The shear viscosity may range from about 0.2 to about 1.4 Pas, about 0.4 to about 1.2 Pas, about 0.6 to about 1.0 Pas, or about 0.8 Pas. As shown, the ROI 116 may comprise a portion of a blood vessel 119 in some examples. The settings of the array 112 can be preset for performing contrast imaging and may be adjustable. A variety of transducer arrays may be used, e.g., convex or phased arrays, including the C5-1 broadband curved array sold by Koninklijke Philips N.V. The number and arrangement of transducer elements included in the sensor array 112 may vary in different examples.

As further shown, the ultrasound data acquisition unit 110 can include a beamformer 120, which may comprise a microbeamformer or a combination of a microbeamformer and a main beamformer, coupled to the sensor array 112. The beamformer 120 may appropriately delay echo signals from the different transducer elements and combine them to form a sequence of coherent echo signals along the beam form from shallow to deeper depths. The functions of the beamformer 120 may vary in different ultrasound probe varieties. For example, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some embodiments, the beamformer 120 may include a microbeamformer operating on groups of sensor elements for both transmit and receive beamforming, coupled to a main beamformer which operates on the group inputs and outputs for both transmit and receive beamforming, respectively. In particular embodiments, the microbeamformer may control the transmission and reception of signals by the transducer elements in the array.

Multiple pulses 114 can be transmitted in each beam direction from the array 112 using different modulation techniques, resulting in the reception of multiple echoes for each scanned point in the image field. The echoes corresponding to a common spatial location may be referred to as an ensemble of echoes, which may be stored in an ensemble memory 121, from which they can be retrieved and processed together.

The data acquisition unit 110 may also include a signal processor 122, which can be configured to decipher nonlinear signals (derived from microbubbles) from linear signals (derived from tissues) received at the array 112. The signal processor 122 may be communicatively, operatively and/or physically coupled with the sensor array 112 and/or the beamformer 120. In the example shown in FIG. 1, the signal processor 122 is included as an integral component of the data acquisition unit 110, but in other examples, the signal processor 122 may be a separate component. In some examples, the received signals can be selectively masked by a clutter filter or phase mask 124, which may constitute a sub-component or module of the signal processor 122, such that linear, tissue-derived signals are suppressed, leaving only nonlinear signals derived from microbubbles. By removing tissue-derived noise, the SNR of the microbubble-based signals may be further enhanced. Embodiments may also include a post-masking processor 126 configured to further enhance the non-masked, i.e., microbubble-based, signals.

The microbubble-derived echoes can be further processed to form two dimensional, three dimensional, spectral, parametric, other desired image types by image processor 128. The resulting images 130 can then be displayed on a graphical user interface 132. The image processor 128 can be configured to organize and display B-mode and/or Doppler image data to form live ultrasound images of the region of interest 116. In some examples, the image processor 128 can be configured to generate images of the phase-shift magnitude(s) detected during or after pulse transmission. The graphical user interface 132 may be configured to display one or more user notifications and/or elements 134 selectable by a user. In some examples, the elements 134 can include a "contrast enhancement" graphic 136, which upon selection by a user, can invoke the selective suppression of non-microbubble based signals according to the implementations described herein.

Figure 2A:
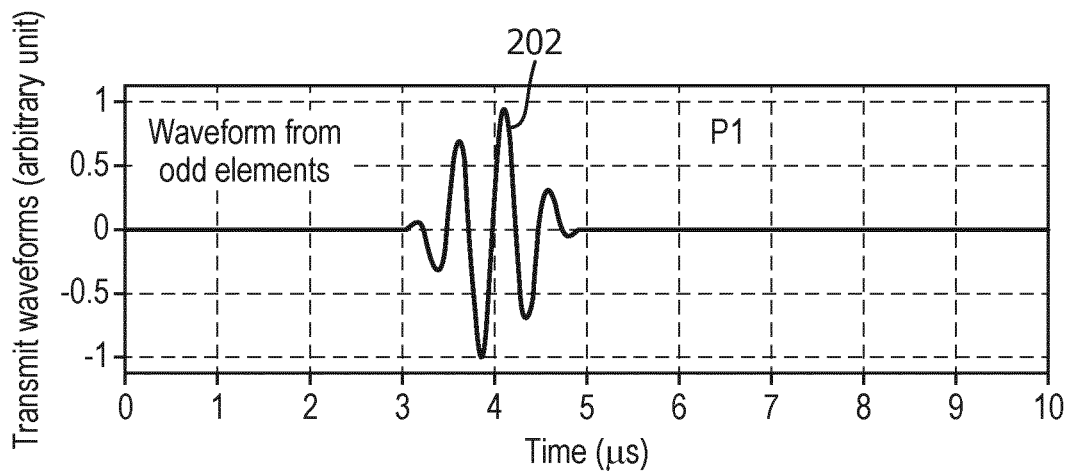
FIG. 2A is a graphical representation of an initiation pulse transmitted in accordance with an embodiment of the present disclosure.
Figure 2B:
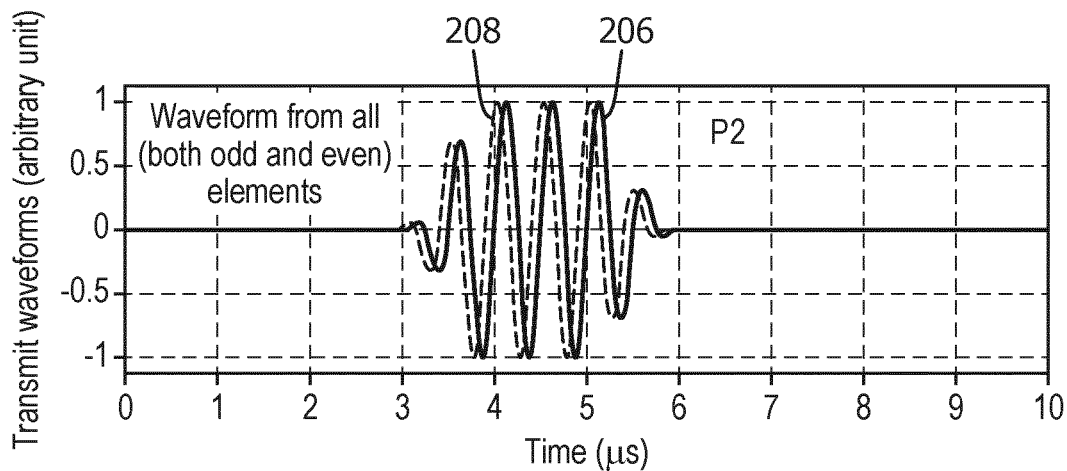
FIG. 2B is a graphical representation of a summation pulse transmitted in accordance with an embodiment of the present disclosure.
Figure 2C:
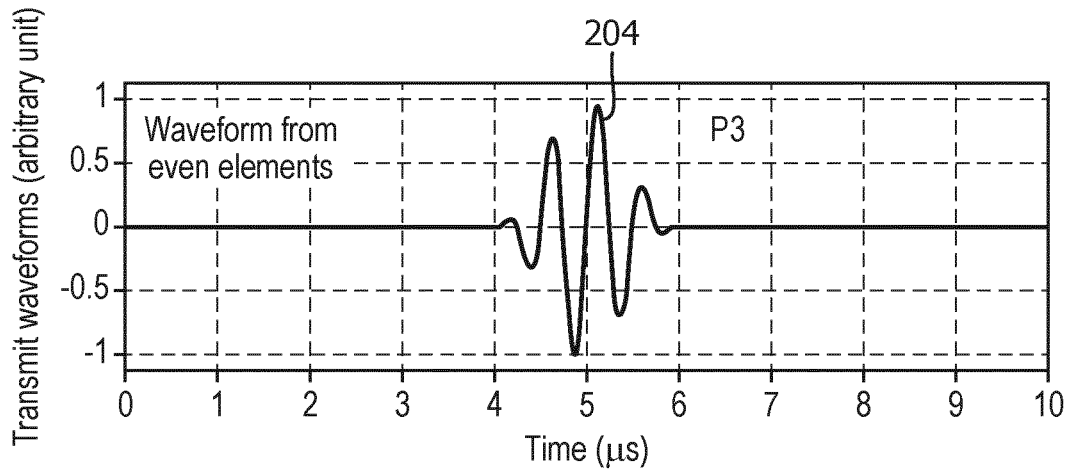
FIG. 2C is a graphical representation of a detection pulse transmitted in accordance with an embodiment of the present disclosure.

FIG. 2 illustrates an example of an initiation pulse 202 transmitted alone (P1), a detection pulse 204 transmitted alone (P3), and a summation pulse 206 comprised of the initiation and detection pulses transmitted together (P2). These pulses may be transmitted by a transducer array to implement the contrast imaging techniques described herein. As shown in FIG. 2A, the initiation pulse 202 may comprise a relatively short, e.g., about 4 cycles, sinusoidal waveform with a frequency of about 2 MHz. The specific pulse parameters may vary, provided the initiation pulse 202 is configured to initiate the targeted microbubbles into resonant oscillation. The initiation pulse 202 may be transmitted from only a subset of array elements in some embodiments. For example, the initiation pulse 202 may be transmitted only from the odd elements of the transducer array, or only the even elements of the array, or in the case of matrix array probes, one or more specific patches of elements. As shown in FIG. 2C, the detection pulse 204 can be transmitted from a separate subset of transducer array elements, such as only the even elements, only the odd elements, or non-overlapping patches of elements, about 2 cycles (or 1 to 2 microseconds) after transmission of the initiation pulse 202, although the time delay between the two pulses may vary. The array elements activated to emit the detection pulse 204 may consist of the elements not activated to emit the initiation pulse 202.

FIG. 2B illustrates an example of a third pulse, summation pulse 206, which can be emitted from both of the subsets of array elements used to transmit the initiation pulse 202 and the detection pulse 204. Continuing with the example described above, the combined array subsets may thus include odd and even elements of the array. In various embodiments, the combined subsets can include non-overlapping subsets, complementary apertures, or orthogonal sub-apertures. Shortly after transmission of the initiation pulse 202 within the summation pulse 206, the detection pulse 204 may be transmitted to detect the resonant oscillation of the microbubbles caused by the initiation pulse. For example, if the initiation pulse 202 is emitted from odd-only elements of the array, then the detection pulse 204 can be emitted separately from even-only elements of the array, after a time delay. The summation pulse 206 may comprise an initiation pulse and a detection pulse transmitted nearly simultaneously from the array. Accordingly, example methods may involve the transmission of three different pulses from the transducer array: an initiation pulse, a detection pulse, and a summation pulse. In some examples, a transmit sequence of the pulses may be an initiation pulse, followed by a summation pulse, followed by a detection pulse. Unlike preexisting systems, the amplitudes for the all three pulse types can be similar so that a higher amplitude pulse can be transmitted from each array element, which may improve the SNR acquired in connection with microbubble-based signals. The specific properties of such pulses, e.g., amplitude, frequency, length, etc., may vary.

As further shown in FIG. 2B, the summation pulse 206 may be distorted in amplitude due to imaging system limitations such as transmit circuitry infidelity and mechanical and/or electrical coupling between the subsets of elements constituting the transducer array. As a result, a distorted summation pulse 208 may be emitted from the transducer array. The degree of distortion may vary depending on the specific transducer employed and/or the specific array elements activated to generate the different pulses. In some examples, a decrease in vibration amplitude from odd elements and a concomitant increase in vibration amplitude from even elements may occur as a result of simultaneous activation of both array subsets, e.g., odd and even elements. Amplitude distortion of the summation pulse may result in incomplete suppression of tissue-derived signals (as shown in FIG. 3D).

Figure 3A:
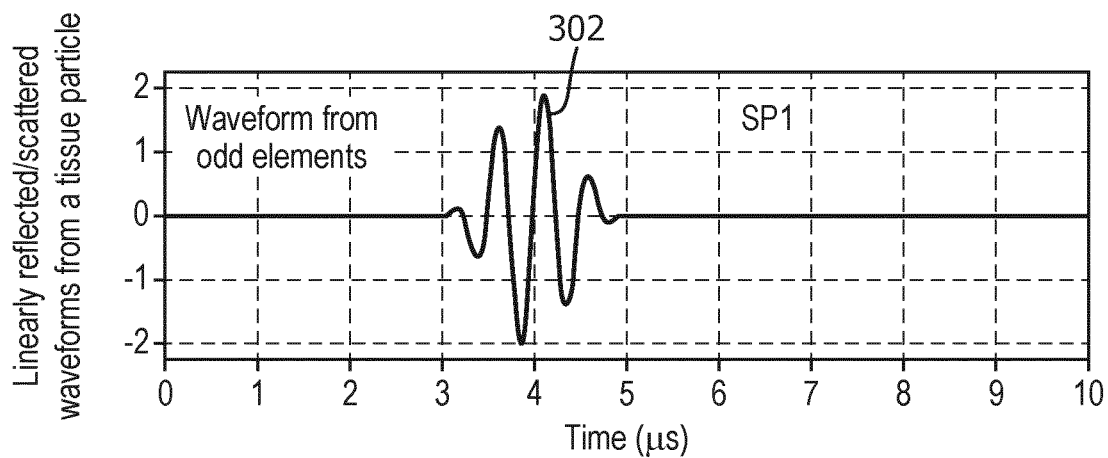
FIG. 3A is a graphical representation of an initiation signal acquired from a primarily linear scatterer in accordance with an embodiment of the present disclosure.
Figure 3B:
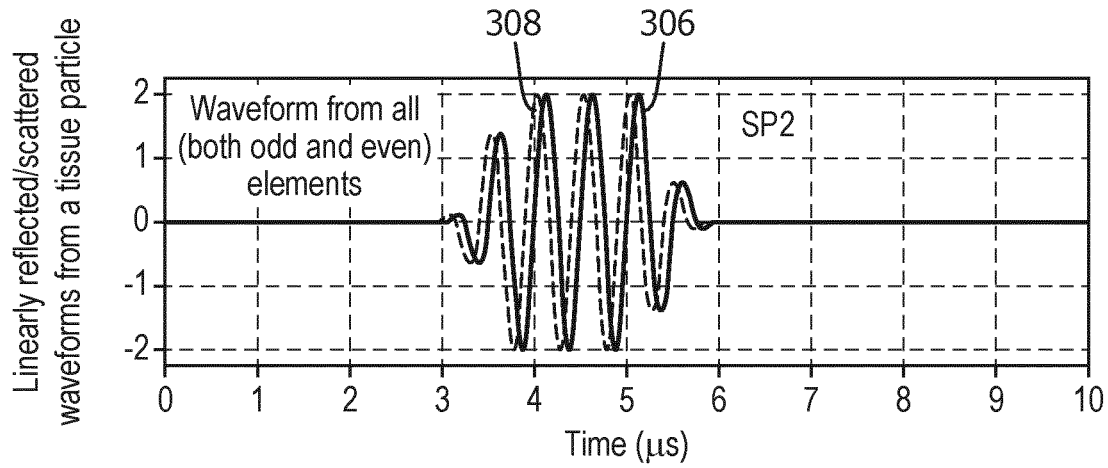
FIG. 3B is a graphical representation of a summation signal acquired from a primarily linear scatterer in accordance with an embodiment of the present disclosure.
Figure 3C:
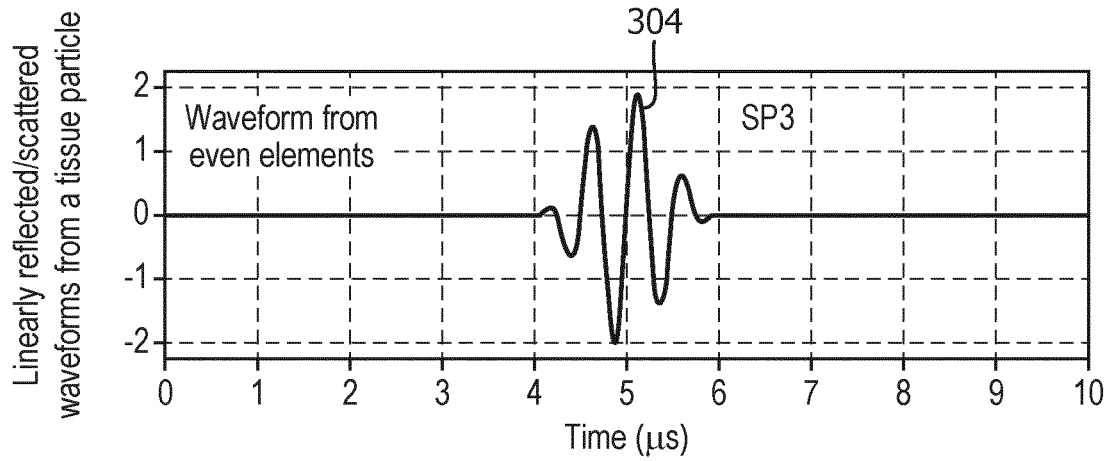
FIG. 3C is a graphical representation of a detection signal acquired from a primarily linear scatterer in accordance with an embodiment of the present disclosure.
Figure 3D:
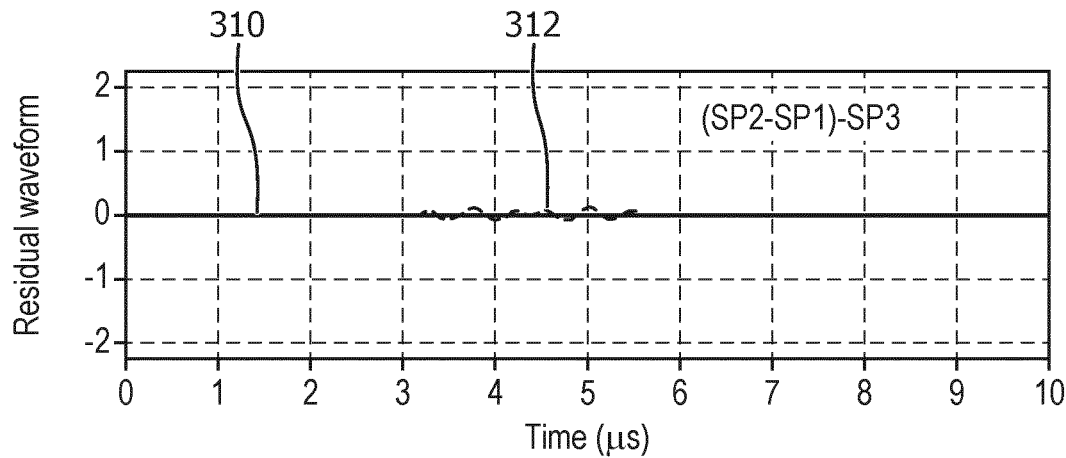
FIG. 3D is a graphical representation of a residual signal acquired from a primarily linear scatterer in accordance with an embodiment of the present disclosure.

The reflected and/or scattered signals from mostly-linear scatterers, such as tissue, generated in response to the pulses of FIGS. 2A-2C are shown in FIGS. 3A-3C, each of which may be acquired by transmitted imaging pulses from the transducer array. The initiation signal 302 derived from the initiation pulse (SP1) is shown in FIG. 3A, the detection signal 304 derived from the separately transmitted detection pulse (SP3) is shown in FIG. 3C, and the summation signal 306 derived from the summation pulse (SP2) is shown in FIG. 3B, as is a distorted summation signal 308 derived from the distorted summation pulse. As shown, the linear tissue-derived signals 302-306 may be nearly identical to the transmitted pulses 202-206. Consequently, the residual signal 310 formed by subtracting the initiation signal 302 and detection signal 304 from the summation signal 306 may be completely suppressed for tissue-derived signals, as shown in FIG. 3D. Notably, however, the residual signal 312 formed by subtracting the initiation signal 302 and detection signal 304 from the distorted summation signal 308 may be incompletely suppressed, even for tissue, due to imaging system limitations such as imperfect coupling between the non-overlapping subsets of elements of the transducer array.

Figure 4A:
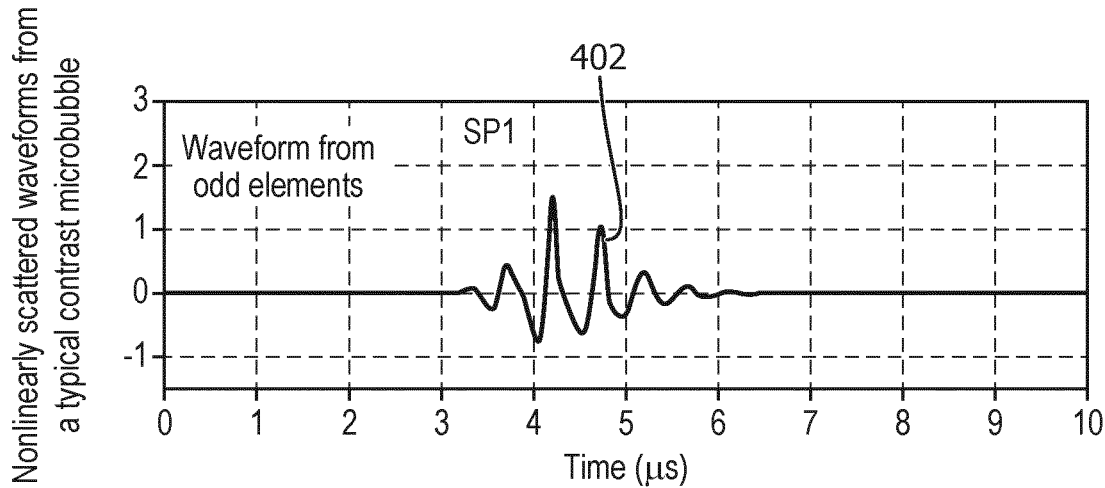
FIG. 4A is a graphical representation of an initiation signal acquired from a nonlinear scatterer in accordance with an embodiment of the present disclosure.
Figure 4B:
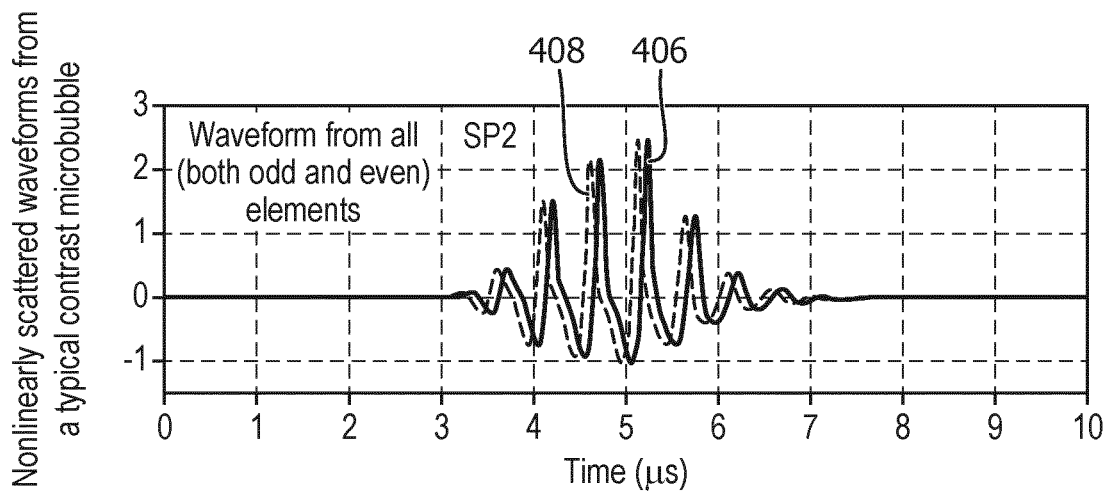
FIG. 4B is a graphical representation of a summation signal acquired from a nonlinear scatterer in accordance with an embodiment of the present disclosure.
Figure 4C:
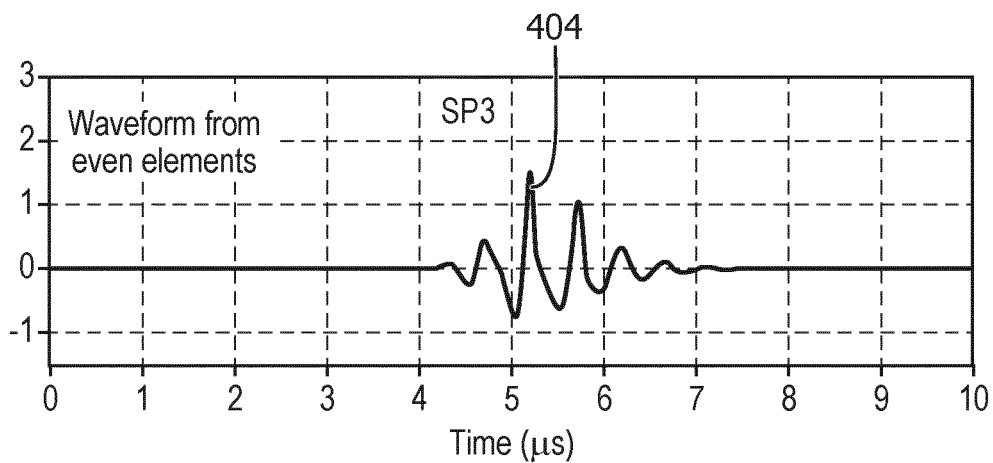
FIG. 4C is a graphical representation of a detection signal acquired from a nonlinear scatterer in accordance with an embodiment of the present disclosure.
Figure 4D:
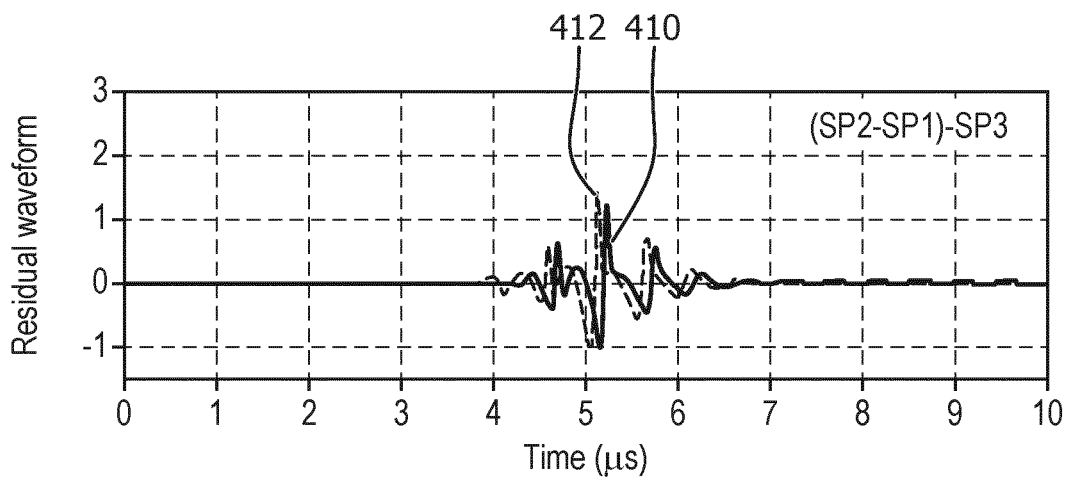
FIG. 4D is a graphical representation of a residual signal acquired from a nonlinear scatterer in accordance with an embodiment of the present disclosure.

By contrast, the reflected and/or scattered signals from nonlinear scatterers, such as microbubbles, generated in response to the pulses of FIGS. 2A-2C are shown in FIGS. 4A-4D. The initiation signal 402 derived from the initiation pulse, which may exhibit fundamental and harmonic content, is shown in FIG. 4A, the detection signal 404 derived from the detection pulse is shown in FIG. 4C, and the summation signal 406 derived from the summation pulse is shown in FIG. 4B, as is the distorted summation signal 408 derived from the distorted summation pulse. As shown, the microbubble-derived signals 402-406 are noticeably different than the transmitted pulses 202-206 due to nonlinear signal scattering caused by the microbubbles in resonance. The residual signal 410 formed by subtracting the initiation signal 402 and detection signal 404 from the summation signal 406 is not suppressed, and neither is the residual signal 412 formed using the distorted summation signal 408. The amplitude changes embodied in the microbubble-derived signals relative to the original pulses may be utilized to distinguish microbubble-derived signals from tissue-derived signals, but such a technique, alone, may not be entirely effective. For instance, the overlapping amplitudes of the tissue- and microbubble-based signals may interfere with efforts to filter the tissue-derived signals from the microbubble-based signals. In addition, the tissue-based residual signal 312 remaining due to imperfect coupling between separate transducer elements may be difficult to disentangle from the microbubble-based residual signals 410, 412.

To distinguish tissue-derived signals from microbubble-derived signals more effectively, systems herein are configured to detect the phase shift caused by an initiation pulse, i.e., after resonant microbubbles are initiated into nonlinear oscillation. In some examples, phase shift detection may involve comparing the summation of initiation and detection signals (derived from separately transmitted initiation and detection pulses) in phase against summation signals (derived from the summation pulses formed by initiation and detection pulses transmitted with a small delay therebetween), for example as shown in FIGS. 5A-5C and FIGS. 6A-6C.

Figure 5A:
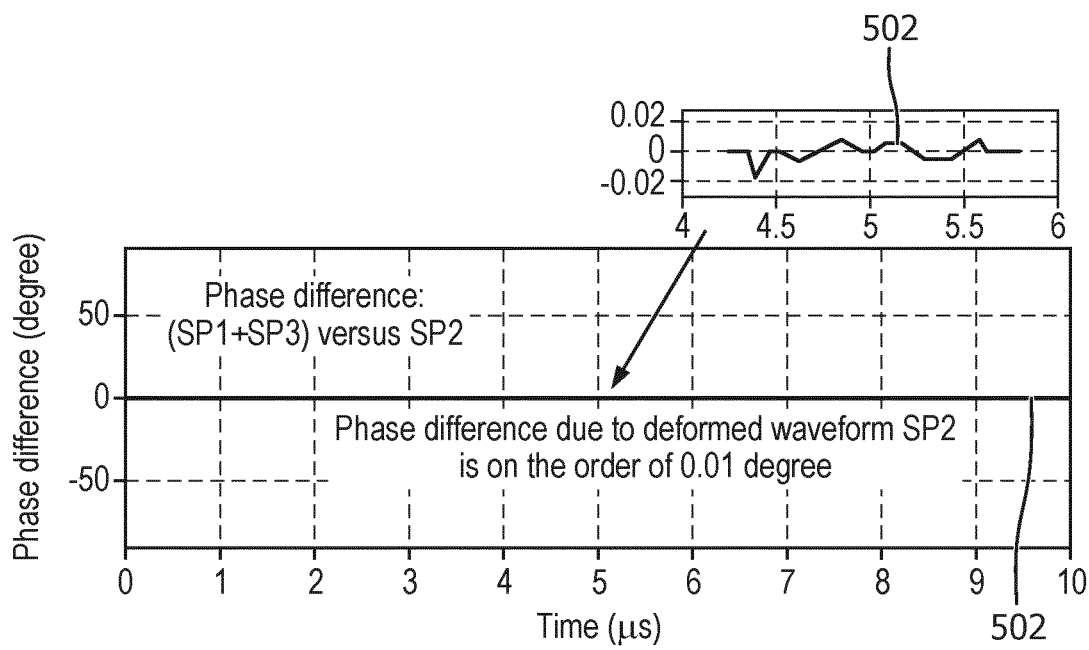
FIG. 5A is a graphical representation of phase shift detected within linear signals in accordance with an embodiment of the present disclosure.
Figure 5B:
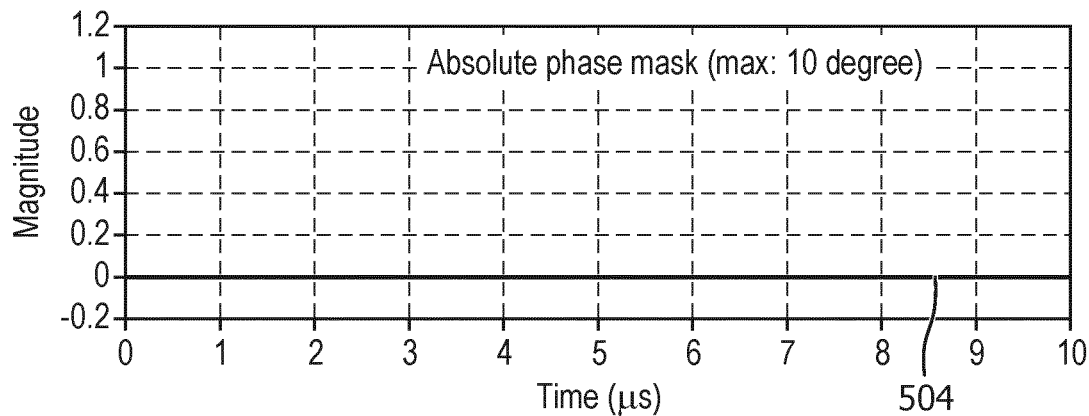
FIG. 5B is a graphical representation of the phase shift of FIG. 5A after application of a phase mask in accordance with an embodiment of the present disclosure.
Figure 5C:
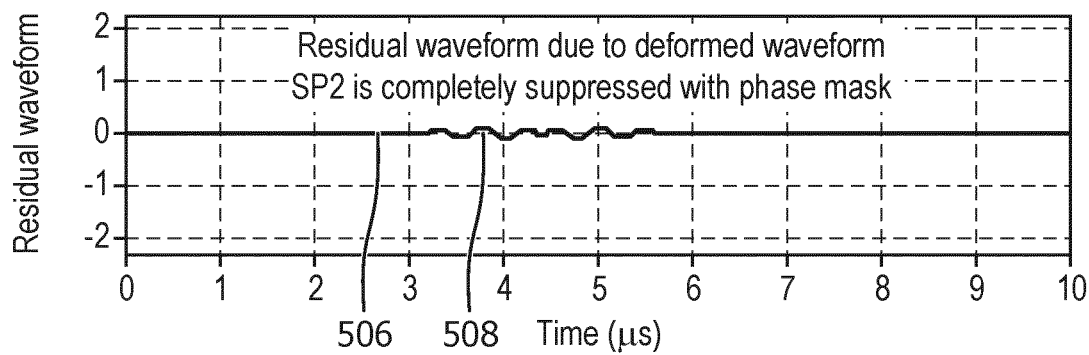
FIG. 5C is a graphical representation of the residual signal of FIG. 3D before and after application of the phase mask in accordance with an embodiment of the present disclosure.

FIG. 5A shows the phase difference 502 exhibited by tissue-derived signals identified by summing the initiation signal 302 with the detection signal 304, and comparing the resulting sum in phase against the distorted summation signal 308. As shown, the phase difference 502 is on the order of only about 0.01 degrees for tissue-derived signals, which may be nearly undetectable. To remove the signals having such an insignificant phase change, thereby effectively filtering tissue-derived signals from the total collection of received signals, systems herein can include a phase mask, such as the phase mask 124 depicted in FIG. 1. The phase mask may be configured to mask or remove all signals having a detected phase shift below a certain threshold. For example, FIG. 5B illustrates the remaining phase shift 504 after applying a phase mask programmed with a 10-degree threshold. As shown, the slight phase shift depicted in FIG. 5A is completely masked. By identifying and masking the tissue-derived signals in this manner, the distortion-induced residual signals 506 associated with tissue-based signals can also be masked, leaving a fully suppressed residual signal 508, as shown in FIG. 5C. The specific magnitude of the threshold applied by the phase mask may vary, ranging from about 1 to about 50 degrees in various embodiments. In addition or alternatively, detected phase shift magnitudes and/or phase differences may be displayed for user review.

Figure 6A:
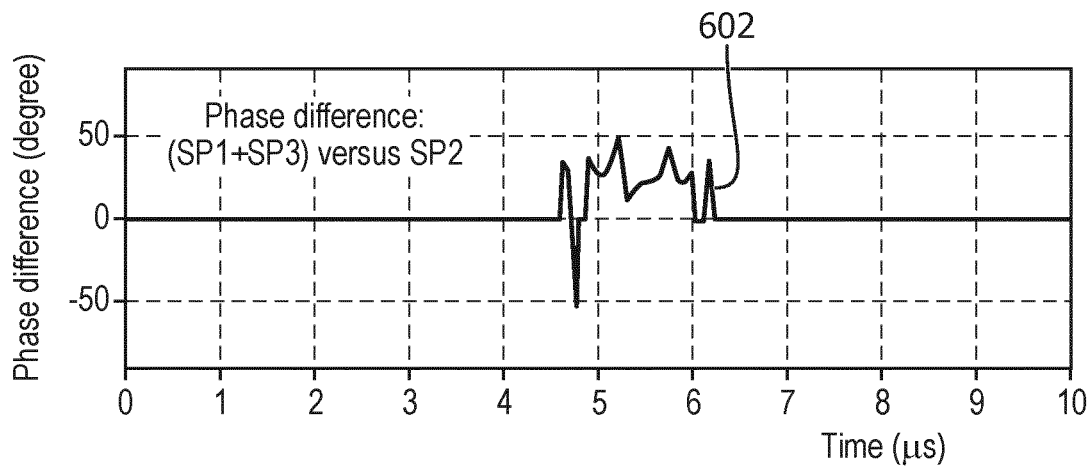
FIG. 6A is a graphical representation of phase change detected within nonlinear signals in accordance with an embodiment of the present disclosure.
Figure 6B:
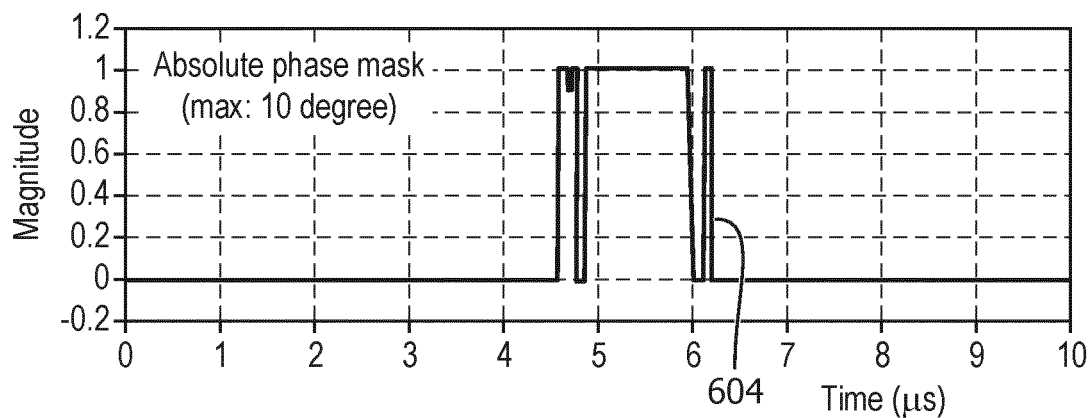
FIG. 6B is a graphical representation of the phase shift of FIG. 6A after application of a phase mask in accordance with an embodiment of the present disclosure.
Figure 6C:
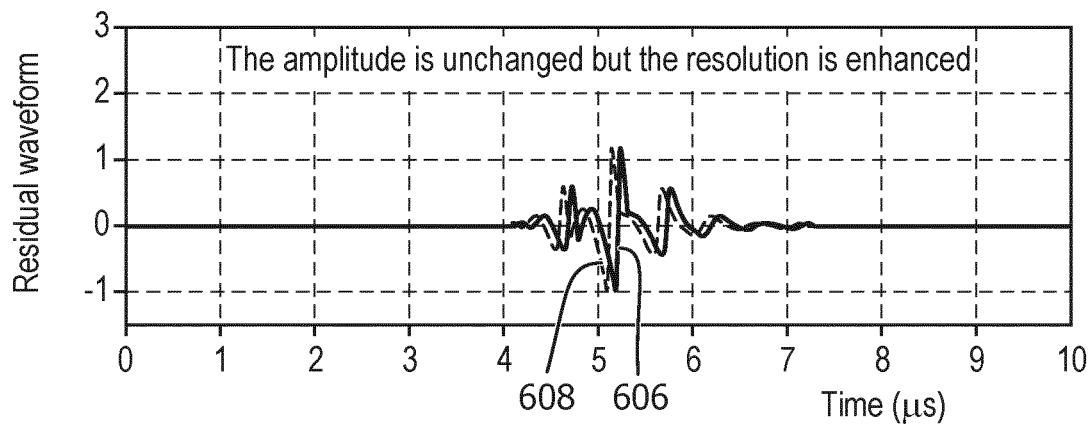
FIG. 6C is a graphical representation of the residual signal of FIG. 4D before and after application of the phase mask in accordance with an embodiment of the present disclosure.

FIG. 6A shows the phase difference 602 exhibited by microbubble-derived signals identified by summing the initiation signal 402 with the detection signal 404, and comparing the resulting sum in phase against the distorted summation signal 408. As shown, phase differences 602 of nearly 50 degrees may be detected for the microbubble-derived signals, each of which remains in the collection of filtered signals 604 after applying the same phase mask with a programmed 10-degree threshold in FIG. 6B. The microbubble-based residual signal 606 may also be preserved, i.e., not masked, and may even exhibit improved resolution, as shown by the filtered, microbubble-based residual signal 608 shown in FIG. 6C. As further shown in FIG. 6C, the filtered, microbubble-based residual signal 608 may have the same amplitude as the pre-filtered signal 606, but may be reduced in length by the phase mask due to masking of signals exhibiting smaller phase shifts, especially near the beginning and end of the signal. The resolution may be determined by the effective length of the detection pulse, and motion artefacts can be minimized by replacing the scattered initiation pulse (SP1) with Equation 1.1 and the scattered detection pulse (SP3) with Equations 1.1 and 1.2, respectively:

$$0.5*SP1(t)+0.5*SP3(t-2T) \tag{Equation 1.1}$$

$$0.5*SP1(t+2T)+0.5*SP3(t) \tag{Equation 1.2}$$

where t represents time and T represents the period.

Figure 7:
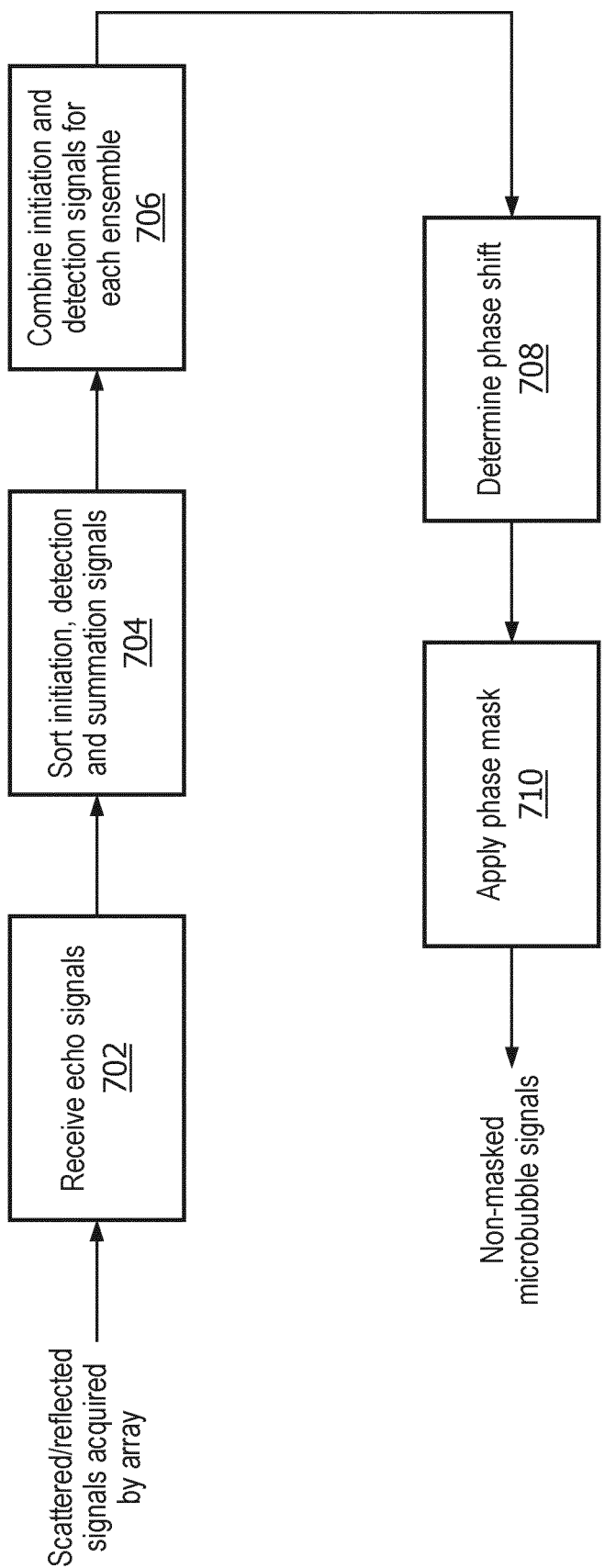
FIG. 7 is a flow diagram illustrating the operational architecture of the signal processor of FIG. 1 in accordance with an embodiment of the present disclosure.

FIG. 7 is a flow diagram illustrating the operational architecture of a signal processor described herein, such as signal processor 122 included in FIG. 1. In box 702, the signal processor may receive scattered and/or reflected echo signals initially detected by an ultrasound transducer array and beamformed by a beamformer. The received signals may include one or more ensembles of echoes, each ensemble comprising an initiation signal, detection signal, summation signal and/or in some examples a distorted summation signal, derived from a common spatial location within the ROI. The signals may be derived from various features, including tissue or microbubbles. As shown in box 704, a sorting module of the signal processor may sort the signals within each ensemble based on signal type, such that initiation, detection and summation echo signals are identified and output into a summing module. As shown in box 706, the summing module of the signal processor may combine the initiation and detection signals together and output combined initiation and detection signal ensembles to further processing blocks of the signal processor, such as a phase shift detection module. In box 708, the phase shift detection module may compare the combined initiation and detection signal ensembles in phase against the summation echo signal ensembles, thereby determining the existence and/or degree of a phase shift between the signals derived from separately transmitted pulses and the signal derived from a summation pulse. In embodiments in which a technique other than phase shift detection is used, the mask may be computed by coupling the sorted signals to a different processing block such as an amplitude determination block or other. In box 710, a masking module, e.g., phase mask 124, may remove or mask signals based on the magnitude of the detected phase shift associated with the signals. In some examples, the masking module may apply a masking threshold and remove or mask all signals having phase shifts below the threshold. The remaining signals, which may consist of microbubble-based signals, only, may then be transmitted to one or more additional processors, such as post-masking processor 126 and/or image processor 128, for supplemental filtering and display.

Figure 8:
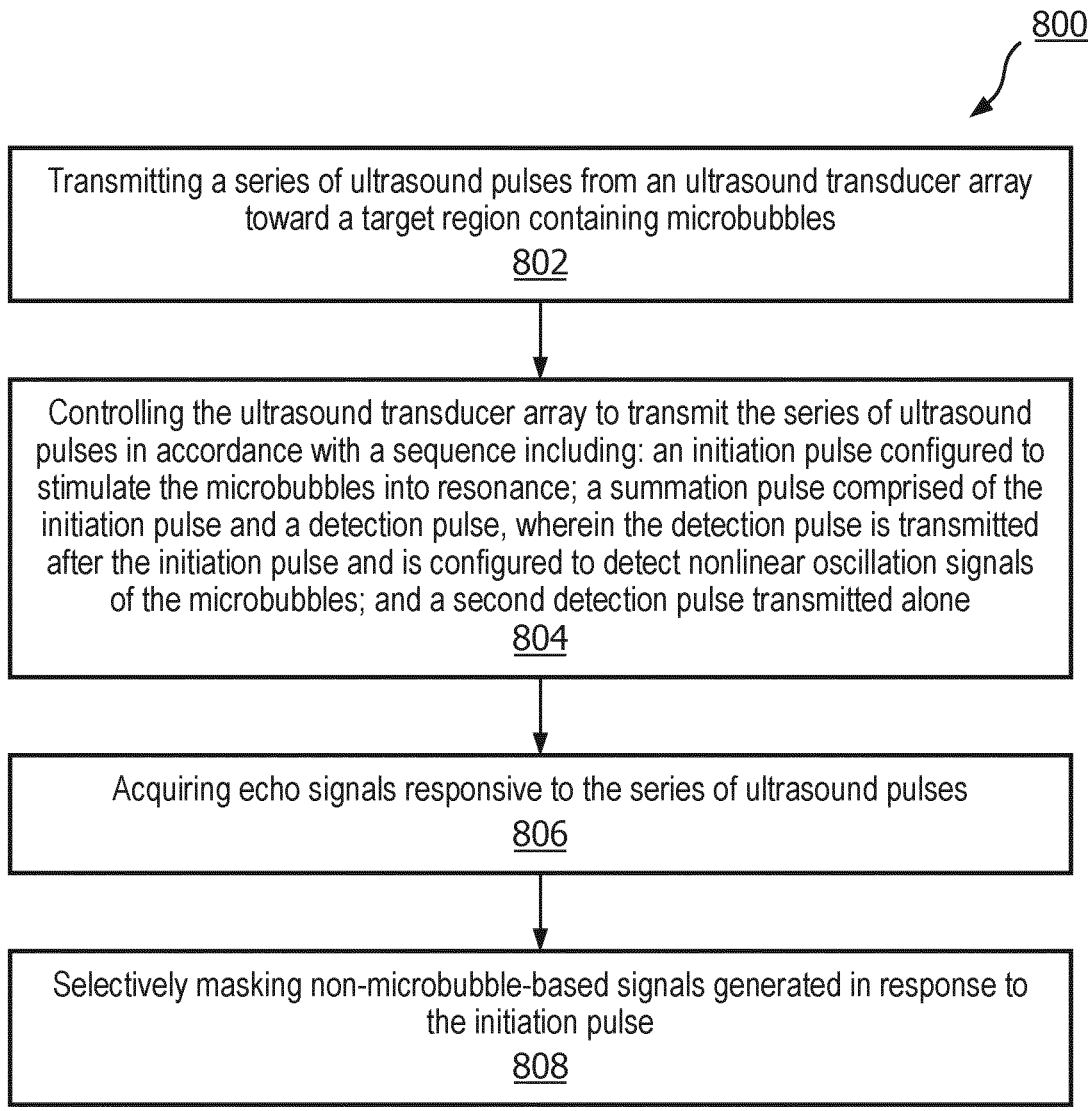
FIG. 8 is a flow diagram of a method of contrast imaging performed in accordance with an embodiment of the present disclosure.

FIG. 8 is a flow diagram of a method of contrast imaging performed in accordance with principles of the present disclosure. The example method 800 shows the steps that may be utilized, in any sequence, by the systems and/or apparatuses described herein for imaging a region of interest containing microbubble contrast agents, and filtering non-microbubble-based signals from microbubble-based signals. The method 800 may be performed by an ultrasound imaging system, such as system 100, or other systems including, for example, a mobile system such as LUMIFY by Koninklijke Philips N.V. ("Philips"). Additional example systems may include SPARQ and/or EPIQ, also produced by Philips.

In the embodiment shown, the method beings at block 802 by "transmitting a series of ultrasound pulses from an ultrasound transducer array toward a target region containing microbubbles."

At block 804, the method involves "controlling the ultrasound transducer array to transmit the series of ultrasound pulses in accordance with a sequence including: an initiation pulse configured to stimulate the microbubbles into resonance; a summation pulse comprised of the initiation pulse and a detection pulse, wherein the detection pulse is transmitted after the initiation pulse and is configured to detect nonlinear oscillation signals of the microbubbles; and a second detection pulse transmitted alone."

At block 806, the method involves "acquiring echo signals responsive to the series of ultrasound pulses."

At block 808, the method involves "selectively masking non-microbubble-based signals generated in response to the initiation pulse."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   an ultrasound transducer array configured to acquire echo signals responsive to a series of ultrasound pulses transmitted toward a target region containing microbubbles;
   a controller configured to control the ultrasound transducer array to transmit the series of ultrasound pulses in accordance with a sequence including:

a first initiation pulse configured to stimulate the microbubbles into non-linear oscillation;

a first detection pulse configured to detect nonlinear oscillation signals of the microbubbles caused by the first initiation pulse, wherein the first detection pulse is generated a first time interval after the first initiation pulse; and a summation pulse comprised of a second initiation pulse and a second detection pulse, wherein the second detection pulse is transmitted a second time interval after the second initiation pulse, and wherein the second time interval is less than the first time interval; and one or more signal processors in communication with the ultrasound transducer array and configured to selectively mask non-microbubble-based signals, wherein selectively masking the non-microbubble based signals comprises masking echo signals derived from the first initiation pulse, the first detection pulse, and the summation pulse, the echo signals exhibiting phase shifts below a phase shift threshold.

2. The ultrasound imaging system of claim 1, wherein the one or more signal processors are configured to determine phase shifts exhibited by the echo signals.

3. The ultrasound imaging system of claim 2, wherein determining the phase shifts exhibited by the echo signals comprises comparing a first signal and a second signal, wherein the first signal comprises a summation of an initiation signal based on the first initiation pulse and a detection signal based on the first detection pulse, and wherein the second signal is based on the summation pulse.

4. The ultrasound imaging system of claim 1, wherein the phase shift threshold is a value selected from a range of greater than or equal to one degree and less than or equal to 50 degrees.

5. The ultrasound imaging system of claim 1, wherein the first initiation pulse and the second initiation pulse are transmitted from a first subset of elements of the ultrasound transducer array.

6. The ultrasound imaging system of claim 5, wherein the first detection pulse and the second detection pulse are transmitted only from a second subset of elements of the ultrasound transducer array that does not overlap with the first subset of elements.

7. The ultrasound imaging system of claim 1, wherein the second time interval is no more than 2 microseconds.

8. The ultrasound imaging system of claim 1, further comprising an image processor configured to produce an ultrasound image of the target region based on the echo signals acquired by the ultrasound transducer array.

9. The ultrasound imaging system of claim 1, further comprising a graphical user interface configured to display the ultrasound image of the target region.

10. The ultrasound imaging system of claim 1, wherein selectively masking the non-microbubble-based signals includes removing residual echo signals generated responsive to at least some ultrasound pulses of the a series of ultrasound pulses, and wherein the at least some ultrasound pulses are generated by non-overlapping elements of the ultrasound transducer array.

11. A method of ultrasound imaging, the method comprising:

transmitting a series of ultrasound pulses from an ultrasound transducer array toward a target region containing microbubbles;

controlling the ultrasound transducer array to transmit the series of ultrasound pulses in accordance with a sequence including:
a first initiation pulse configured to stimulate the microbubbles into non-linear oscillation;
a first detection pulse configured to detect nonlinear oscillation signals of the microbubbles caused by the first initiation pulse, wherein the first detection pulse is generated a first time interval after the first initiation pulse; and
a summation pulse comprised of a second initiation pulse and a second detection pulse, wherein the second detection pulse is transmitted a second time interval after the second initiation pulse, and wherein the second time interval is less than the first time interval;

acquiring echo signals responsive to the series of ultrasound pulses; and selectively masking non-microbubble-based signals, wherein selectively masking the non-microbubble-based signals comprises masking echo signals derived from the first initiation pulse, the first detection pulse, and the summation pulse, the echo signals exhibiting phase shifts below a phase shift threshold.

12. The method of claim 11, wherein selectively masking non-microbubble-based signals comprises determining phase shifts exhibited by the echo signals.

13. The method of claim 12, wherein determining the phase shifts exhibited by the echo signals comprises comparing a first signal and a second signal, wherein the first signal comprises a summation of an initiation signal based on the first initiation pulse and a detection signal based on the first detection pulse, and wherein the second signal is based on the summation pulse.

14. The method of claim 11, wherein the first initiation pulse and the second initiation pulse are transmitted from a first subset of elements of the ultrasound transducer array.

15. The method of claim 14, wherein the first detection pulse and the second detection pulse are transmitted from a second subset of elements of the ultrasound transducer array that does not overlap with the first subset.

16. The method of claim 11, further comprising producing an ultrasound image of the target region based on the echo signals acquired by the ultrasound transducer array after selectively masking the non-microbubble-based signals.

17. A non-transitory computer-readable medium comprising executable instructions, which when executed cause a processor of a medical imaging system to perform the method of claim 11.

* * * * *